United States Patent
Song et al.

(10) Patent No.: US 9,575,186 B2
(45) Date of Patent: Feb. 21, 2017

(54) MULTI-SEGMENT RECONSTRUCTION

(75) Inventors: Xiyun Song, Santa Clara, CA (US);
Zuo Zhao, Palo Alto, CA (US);
Jinghan Ye, Fremont, CA (US);
Lingxiong Shao, Saratoga, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1070 days.

(21) Appl. No.: 12/812,040

(22) PCT Filed: Jan. 7, 2009

(86) PCT No.: PCT/IB2009/050039
§ 371 (c)(1),
(2), (4) Date: Jul. 8, 2010

(87) PCT Pub. No.: WO2009/090571
PCT Pub. Date: Jul. 23, 2009

(65) Prior Publication Data
US 2010/0278412 A1 Nov. 4, 2010

Related U.S. Application Data

(60) Provisional application No. 61/022,012, filed on Jan. 18, 2008.

(51) Int. Cl.
*G01T 1/164* (2006.01)
*A61B 6/03* (2006.01)
(Continued)

(52) U.S. Cl.
CPC ............ *G01T 1/1642* (2013.01); *A61B 6/037* (2013.01); *A61B 6/5241* (2013.01); *G06T 11/005* (2013.01)

(58) Field of Classification Search
CPC ..... G01T 1/1642; A61B 6/037; A61B 6/5241; G06T 11/005
(Continued)

(56) References Cited

U.S. PATENT DOCUMENTS

| 5,311,427 A | 5/1994 | Ichihara |
| 6,114,701 A | 9/2000 | Plummer et al. |

(Continued)

FOREIGN PATENT DOCUMENTS

| JP | 2006054192 A | 2/2006 |
| WO | 0195109 A2 | 12/2001 |

(Continued)

OTHER PUBLICATIONS

Vastenhouw, B., et al.; Submillimeter Total-Body Murine Imagine with U-SPECT-I; 2007; J. Nucl. Med.; 48:487-493.
(Continued)

*Primary Examiner* — Michelle L Le (57) ABSTRACT

A medical imaging system includes a view transformation component (210) and a segment combiner (212). The transformation component (210) transforms projection data in each view of a plurality of individual segments, which each includes at least one view. The transformed projection data for substantially similar views across the plurality of individual segments have a common radius of rotation. The segment combiner (212) combines the transformed projection data to produce a single data set that includes the transformed projection data for each of the views of each of the plurality of individual segments.

10 Claims, 4 Drawing Sheets

(51) Int. Cl.
*A61B 6/00* (2006.01)
*G06T 11/00* (2006.01)

(58) Field of Classification Search
USPC .................................................. 382/128, 131
See application file for complete search history.

(56) References Cited

U.S. PATENT DOCUMENTS

| | | |
|---|---|---|
| 6,177,675 B1 | 1/2001 | Gagnon et al. |
| 6,269,177 B1 | 7/2001 | Dewaele et al. |
| 6,593,576 B2 | 7/2003 | Zeng et al. |
| 7,123,779 B2* | 10/2006 | Beuker et al. ................ 382/294 |
| 8,063,380 B2 | 11/2011 | Levin et al. |
| 2002/0109113 A1 | 8/2002 | Wang et al. |
| 2006/0078082 A1 | 4/2006 | Motomura et al. |
| 2006/0098857 A1 | 5/2006 | Hawman |
| 2006/0124855 A1* | 6/2006 | Gagnon ................... 250/370.09 |
| 2006/0261277 A1 | 11/2006 | D'Ambrosio et al. |
| 2007/0194240 A1 | 8/2007 | Hefetz |
| 2009/0060121 A1 | 3/2009 | Ziegler et al. |
| 2011/0249875 A1* | 10/2011 | Dewaele ...................... 382/128 |

FOREIGN PATENT DOCUMENTS

| | | |
|---|---|---|
| WO | 02065398 A1 | 8/2002 |
| WO | 2004113951 A2 | 12/2004 |

OTHER PUBLICATIONS

Glick, S. J., et al.; A Fast Projector Backprojector Pair for Use in Iterative Reconstruction of SPECT Images; 1994; IEEE; pp. 1576-1580.

* cited by examiner

MULTI-SEGMENT RECONSTRUCTION

CROSS REFERENCE TO RELATED APPLICATIONS

This application claims the benefit of U.S. provisional application Ser. No. 61/022,012 filed Jan. 18, 2008, which is incorporated herein by reference.

The following generally relates to reconstructing multiple segments of projection data having similar views with different radii of rotation. While it is described with particular application to a single photon emission computer tomography (SPECT) scanner, it also amenable to other medical imaging and non-medical imaging applications.

A SPECT system generally includes at least one gamma camera configured to rotate about an examination region and acquire projections for a plurality of projection angles or views in a segment by detecting gamma radiation from radionuclide decay occurring in a region of interest (e.g., an organ, a lesion, etc.) in a subject suitably positioned in the examination region. The gamma camera(s) produces projection data indicative of the detected radiation. A reconstructor reconstructs the projection data to produce volumetric image data. The volumetric image data can be further processed to generate one or more images.

When rotating about the examination region, the location of the at least one gamma camera, with respect to the region of interest, may radially vary between views in the segment depending, for example, on the shape of the subject. As such, the distance between the region of interest and the gamma camera may vary between views. Generally, with respect to a point in the examination region, the spatial resolution depends on the distance from the point to the gamma camera, as well as other characteristics, and typically decreases as a function of increasing distance between the point and the gamma camera. This phenomenon has been referred to depth-dependent resolution variation. A depth-dependent resolution recovery reconstruction algorithm, which takes into account the distance between the region of interest in the subject and the gamma camera, has been used to account for the varying distance.

For some SPECT procedures, such as whole body scans, projections are acquired for multiple substantially contiguous segments, in which each segment covers a different sub-portion of the subject, due to the limited field of view (FOV) of the detectors in the axial direction. For example, acquiring data for a whole body scan may entail acquiring data for three to four substantially contiguous segments that aggregately include projection data that covers the whole body.

As noted above, for a particular segment, the distance between the region of interest and the gamma camera may vary between views in the segment. For a whole body scan, the region of interest may lie along on an imaginary rotation or z-axis that longitudinally extends through the subject and that is generally perpendicular to the face of the gamma camera. As such, for a whole body scan the distance between the axis of rotation and the gamma camera may vary between views in a segment. Moreover, this distance may vary between substantially similar views (having a substantially similar view angle) in different segments since each segment covers a different sub-portion of the subject, which may differ in shape with respect to the sub-portions of the subject covered in the other segments. For example, when using an Automatic Body Contour (ABC) technique, the distance between the axis of rotation and the gamma camera for each view across segments typically is different.

As a consequence, when using a depth-dependent resolution recovery reconstruction algorithm, the projection data for the different segments are reconstructed segment-by-segment since depth-dependent resolution recovery requires that the distance between the axis of rotation and the gamma camera be substantially the same for a particular view across the different segments. As a result, the reconstruction technique for reconstructing different segments for a whole body scan, or other scan in which multiple segments of projection data are acquired, generally includes individually and independently reconstructing each segment, and then suitably combining the reconstructed data for each segment to form a single three-dimensional data set indicative of the whole body.

Unfortunately, a segment-by-segment reconstruction can be inefficient and inconvenient in clinical applications since the operator, for each segment, needs to select the corresponding projection data, load the selected projection data, select the protocol, invoke reconstruction of the loaded data and save the reconstructed data, and, after all of the segments are reconstructed, the operator needs to select, load and combine the reconstructed data, and then save the combined data to generate a single data set covering the whole body. In this workflow, the operator repeats similar steps multiple times, which can be both inefficient and inconvenient. Furthermore, attenuation correcting (via CT-AC) the data further complicates the workflow.

Aspects of the present application address the above-referenced matters and others.

According to one aspect, a medical imaging system includes a view transformation component and a segment combiner. The transformation component transforms projection data in each view of a plurality of individual segments, which each includes at least one view. The transformed projection data for substantially similar views across the plurality of individual segments have a common radius of rotation. The segment combiner combines the transformed projection data to produce a single data set that includes the transformed projection data for each of the views of each of the plurality of individual segments.

In another aspect, a method includes applying a corresponding transformation to projection data in each view in a plurality of individual segments of projection data, wherein the transformation for each of the views transforms the projection data for the corresponding view such that the transformed projection data for the corresponding view has a common radius of rotation across the plurality of segments. The method further includes combining the transformed projection data for each view of each of the plurality of individual segments to produce a single data set that includes the projection data for each of the individual segments, wherein the single data set is stored in a storage device.

In another aspect, a computer readable storage medium contains instructions which, when executed by a computer, cause the computer to perform the steps of: applying a corresponding transformation to projection data in each view in a plurality of individual segments of projection data, wherein the transformation for each of the views transforms projection data for the corresponding view such that the transformed projection data for the corresponding view has a common radius of rotation across the plurality of segments; combining the transformed projection data for each view of each of the plurality of individual segments to produce a single data set that includes the projection data for each of the individual segments; and reconstructing the single data set using a depth-dependent resolution recovery reconstruction algorithm.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
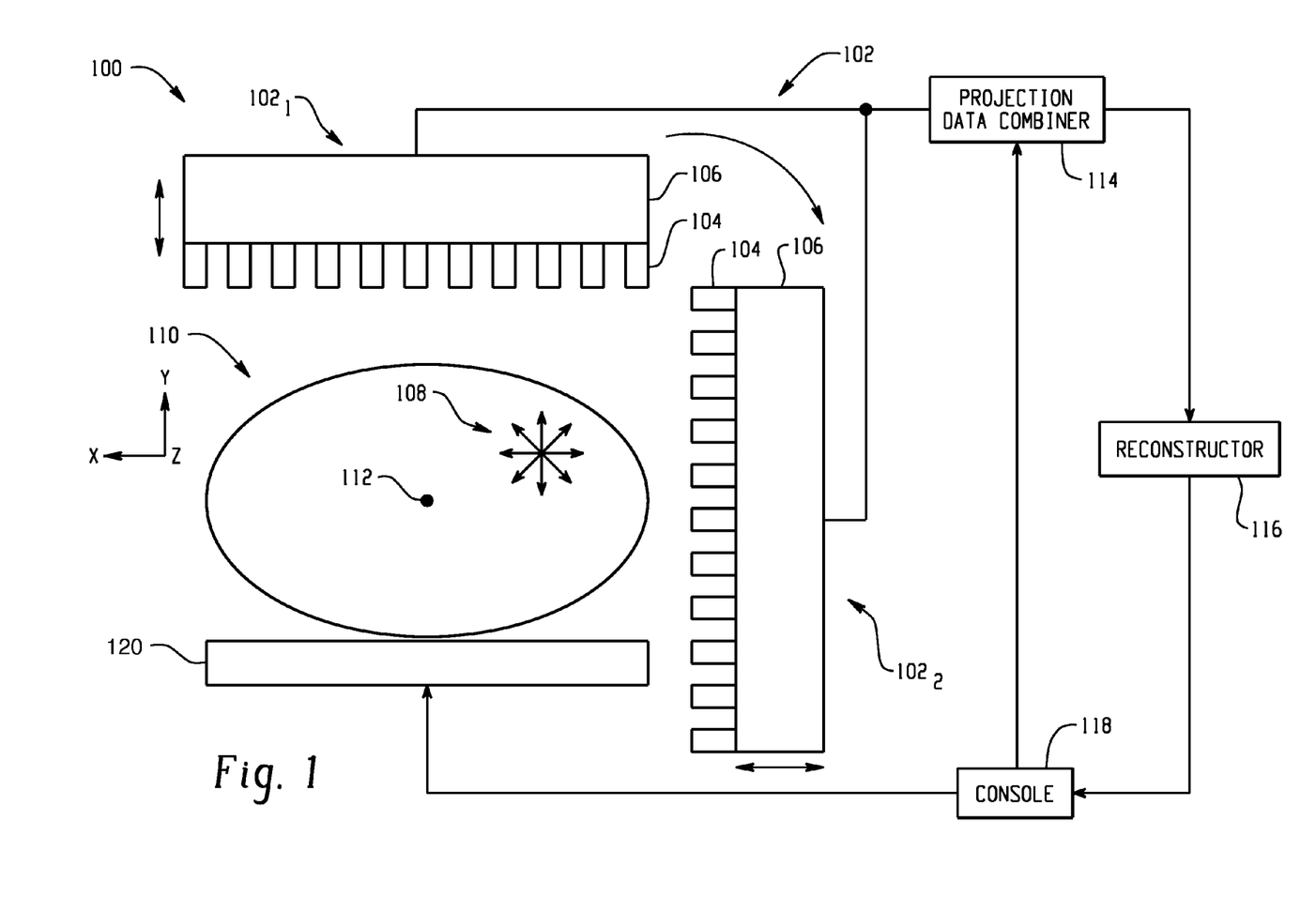
FIG. 1 illustrates an exemplary medical imaging system.

With reference to FIG. 1, a SPECT system 100 includes at least one gamma radiation sensitive detector, such as a gamma camera. The illustrated system 100 includes two gamma cameras 102$_1$ and 102$_2$, collectively referred to herein as gamma cameras 102. Each of the gamma cameras 102 includes a collimator 104 and a photosensor array 106. The collimator 104 is made from lead or the like and includes an array of holes through which gamma photons 108, emanating from an examination region 110 and traversing along directions within a range of angles, pass through. In the illustrated system 100, the photosensor array 106 includes a scintillator in optical communication with an array of photomultiplier tubes (PMTs) or semiconductor photodetectors. In other embodiments, the photosensor array 106 may include a direct conversion detector and other light sensitive detector.

In the illustrated example, the gamma cameras 102$_1$ and 102$_2$ are disposed relative to each other at an angle in the range of roughly ninety (90) degrees to one hundred and two (102) degrees. However, other angles are also contemplated. The gamma cameras 102 are configured to rotate around an examination region 110 and about a longitudinal or z-axis 112, which extends longitudinally through the examination region 110 and perpendicularly with respect to the gamma cameras 102, to acquire projections for plurality of projection angles or views in a segment. One or more drives vary the relative positions of the gamma cameras 102 and an object or subject in the examination region 110, for example, by rotating the gamma cameras 102 about the examination region 110 and/or tangentially or radially moving the gamma cameras 102 with respect to the examination region.

As the gamma cameras 102 rotate, the scintillator 106 receives the gamma photons passing through the collimator holes and produces light in response thereto, and the photosensor arrays 106 generate projection data indicative of the detected gamma photons. The spatial resolution of the data generally depends on the distance from a region of interest in the examination region 110 to the photosensor arrays 106, which is referred to depth-dependent resolution variation. The illustrated example is described in connection with a multi-segment scan such as a whole body scan, with the distance (referred to herein as a radius of rotation, or ROR) being a distance between an axis 112, which extends longitudinally through the examination region 110 and perpendicularly with respect to the gamma cameras 102, and the region of the collimator 104 proximate the examination region 110. In scans such as whole body scans, the ROR between views in a segment and/or the ROR between substantially similar views in different segments may be different.

A projection data combiner 114 combines or "knits" the projection data for different segments together in the projection domain to form a single projection data set that includes projection data from multiple segments. As described in greater detail below, this includes processing the projection data for the different segments such the projection data for substantially similar views in different segments is referenced to a common or reference radius of rotation (ROR$_{ref}$). As such, the combined projection data from different segments can be reconstructed during a single reconstruction, using a depth-dependent resolution recovery reconstruction algorithm. This may improve workflow as compared to reconstructing each segment individually and independently, using a depth-dependent resolution recovery reconstruction algorithm, and then post-processing the reconstructed segments by combining them to form a single volumetric data set. The combined data can be stored in a storage device such a memory, cassette tape, optical disk, magnetic disk, etc.

A reconstructor 116 reconstructs the projection data to generate volumetric or three-dimensional image data indicative of the distribution of radioisotopes emanating from the examination region 110. In one instance, the reconstructor 116 employs an iterative reconstruction algorithm with resolution recovery by modeling depth-dependent collimator-detector response functions (distance dependent resolution models) that compensate for the distance-dependent spatial resolution blurring of the collimators and detectors. In the illustrated example, during the reconstruction the collimator-detector response functions are modeled, collectively at each viewing angle, for each view across segments, which share the reference radius of rotation, ROR$_{ref}$. According to such an approach, increasing the number of iterations tends to improve the spatial resolution of the image as compared to techniques in which the distance dependent detector resolution is not modeled. In other embodiment, other reconstruction algorithms may be used.

A computer serves as an operator console 118. The console 118 includes a human readable output device such as a monitor or display and input devices such as a keyboard and mouse. Software resident on the console 118 allows the operator to view and otherwise manipulate the volumetric image data, for example, through a graphical user interface (GUI). Software resident on the console 118 also allows the operator to control the operation of the system 100 by establishing desired scan protocols, initiating and terminating scans, and otherwise interacting with the scanner 100.

An object support 120 supports an object, such as a human patient, luggage, etc., to be imaged. The object support 120 is configured to move longitudinally in coordination with operation of the system 100 so that an object can be scanned at a plurality of longitudinal locations according to desired scanning trajectories.

Figure 2:
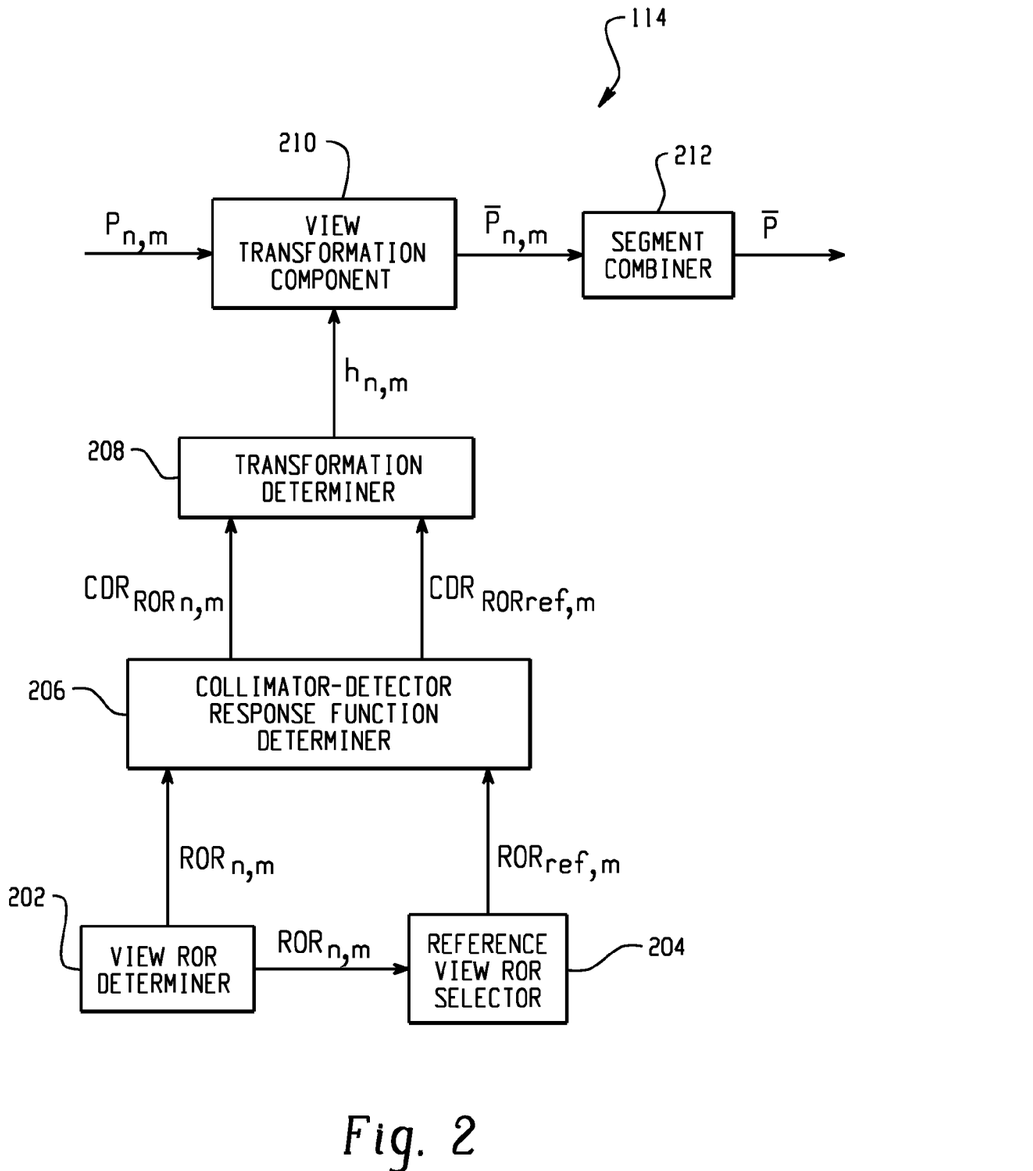
FIG. 2 illustrates an example embodiment of the medical imaging system.

FIG. 2 illustrates an example embodiment of the projection data combiner 114. For this embodiment, assume a study includes N segments of projection data, wherein N is a positive integer equal to or greater than two (2) (e.g., two (2), three (3), four (4), etc.). Also assume that each segment includes M views of data, wherein M is a positive integer such as sixty-four (64), one hundred and twenty-eight (128), etc. As noted above, for total-body scans, the ROR may differ at least for substantially similar views across segments. For this example, assume that each ith view across the N segments have different ROR's.

Figure 3:
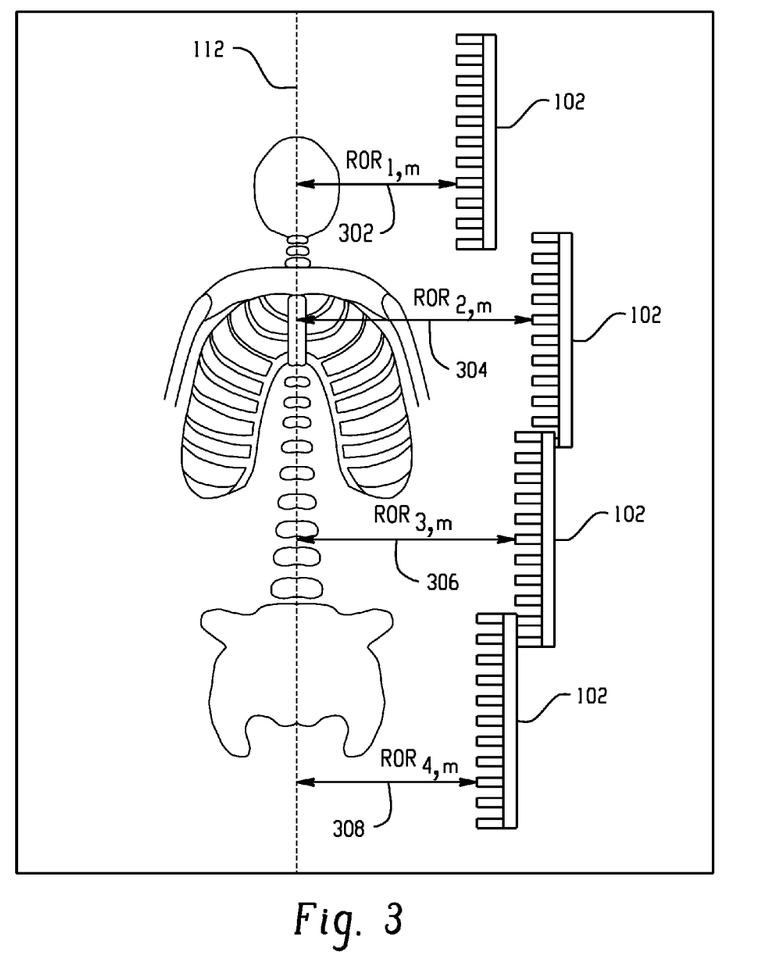
FIG. 3 illustrate an image showing projection data from different segments.

As illustrated, a view ROR determiner 202 determines a ROR$_{n,m}$ for each of the M views for each of the N segments. In the illustrated example, the ROR$_{n,m}$ is based on the distance from the reference line 112 (FIG. 1), which extends along the z-axis through the different segments, to the collimator 104 (FIG. 1). FIG. 3 shows the reference line 112 as well as ROR's respectively for the mth view for segments one through four (1-4), or $ROR_{1,m}$ 302, a $ROR_{2,m}$ 304, a $ROR_{3,m}$ 306, and a $ROR_{4,m}$ 308. Note that in FIG. 3, for each segment the detector may be positioned such a segment slightly overlaps a preceding segment. In other embodiments, there may be more or less overlap, including no overlap.

Returning to FIG. 2, a reference ROR selector 204 selects a reference $ROR_{ref,m}$ for each of the M views used with the N segments. In the illustrated example, the selected reference $ROR_{ref,m}$, for a particular view, is the largest $ROR_{n,m}$ for that view. However, in other embodiments, the reference $ROR_{ref,m}$ may be otherwise selected. For example, the ROR selector 204 may alternatively select a reference $ROR_{ref,m}$, for a particular view, that represents the median ROR, the mean ROR, the smallest ROR, an optimally determined ROR, etc. for that view. In another embodiment, $ROR_{n,m}$ and/or $ROR_{ref,m}$ are known or determined elsewhere. In such an embodiment, the reference ROR selector 204 is omitted.

A collimator-detector response function determiner 206 determines collimator-detector response functions $CDR_{ROR_{n,m}}$ and $CDR_{ROR_{ref,m}}$, which are depth-dependent collimator-detector response functions. In the illustrated example, the $CDR_{ROR_{n,m}}$ and $CDR_{ROR_{ref,m}}$ are respectively determined based on $ROR_{n,m}$ and $ROR_{ref,m}$. For explanatory purposes and sake of brevity, the collimator-detector response functions, $CDR_{ROR_{n,m}}$ and $CDR_{ROR_{ref,m}}$ are described in terms of a Gaussian function, which is often used to describe collimator-detector response functions. However, other function can alternatively be used.

By way of example, given the resolution of a collimator system, its response function CDR can be estimated as shown in Equation 1, which represents a one-dimensional Gaussian function:

$$\frac{1}{2\pi\sigma}\exp\left(-\frac{(x-\mu)^2}{2\sigma^2}\right), \quad \text{Equation 1}$$

wherein σ is equal to $$\frac{FWHM}{2\sqrt{2\ln 2}},$$

and FWHM is the collimator resolution in terms of the Full Width at Half Maximum (e.g, in units of mm). The FWHM can be determined as shown in Equation 2:

$$\frac{ROR+B+C+D}{L}\times 1.05 \times H, \quad \text{Equation 2}$$

wherein B represents a collimator length; C represents a cover thickness; D represents half of the thickness of the crystal; H represents a collimator hole size and L represents an effective collimator length. Equation 2 can be re-written in terms of an attenuation coefficient μ as shown in Equation 3:

$$\frac{ROR+B+C+D}{B-\frac{20}{\mu}}\times 1.05 \times H, \quad \text{Equation 3}$$

wherein L is equal to $$B-\frac{20}{\mu}.$$

As such, both $$FWHM_{CDR_{ROR_{ref,m}}} \text{ and } FWHM_{CDR_{ROR_{n,m}}}$$

can be determined. In another embodiment, $$CDR_{ROR_{n,m}} \text{ and/or } CDR_{ROR_{ref,m}} \text{ or}$$

$$FWHM_{CDR_{ROR_{ref,m}}} \text{ and/or } FWHM_{CDR_{ROR_{n,m}}}$$

are known or determined elsewhere. In such an embodiment, the collimator-detector response function determiner 206 is omitted.

A transformation determiner 208 determines a transformation $h_{n,m}$ for each of the M views for each of the N segments based on the $CDR_{ROR_{n,m}}$ and $CDR_{ROR_{ref,m}}$. For example, in the illustrated embodiment, the transformation $h_{n,m}$ is determined such that is satisfies Equation 4:

$$CDR_{ROR_{n,m}} * h_{n,m} = CDR_{ROR_{ref,m}}. \quad \text{Equation 4}$$

When $ROR_{n,m}$ is smaller than $ROR_{ref,m}$, the effect of transformation $h_{n,m}$ is typically convolution. When $ROR_{n,m}$ is greater than $ROR_{ref,m}$, the effect of transformation $h_{n,m}$ is typically de-convolution. For explanatory purposes and convenience, the following discussion assumes the convolution scenario, i.e. the $ROR_{n,m}$ is smaller than the $ROR_{ref,m}$ and thus the $$FWHM_{CDR_{ROR_{n,m}}}$$

is smaller than the $$FWHM_{CDR_{ROR_{ref,m}}}.$$

Like the collimator-detector response functions, $CDR_{ROR_{q,m}}$, and $CDR_{ROR_{ref,m}}$, the transformation $h_{n,m}$ may be described in terms of a Gaussian function, as described above, or otherwise. $FWHM_h$ can be determined from Equation 5:

$$FWHM_h = \sqrt{FWHM^2_{CDR_{ROR_{ref,m}}} - FWHM^2_{CDR_{ROR_{n,m}}}}, \quad \text{Equation 5}$$

and the transformation $h_{n,m}$ can be determined from Equation 1 above based on the determined $FWHM_h$. In another embodiment, $h_{n,m}$ and/or $FWHM_h$ are known or determined elsewhere. In such an embodiment, the view transformation determiner 208 is omitted.

Another way to look at this is to assume there is a collimator system, imaging an object using two different radii R1 and R2. For convenience, assume R1<R2. These two cases can be treated as two different systems: $S_1$ and $S_2$. $S_1$ has the collimator resolution $FWHM_1$, which can be determined using the above equations, and $S_2$ has the collimator resolution $FWHM_2$, which can also be determined using the above equations. Suppose there is a initial image f, and a function h(x,y) satisfies the following relationship: $f(x,y) \otimes g_1(x,y) \otimes h(x,y) = f(x,y) \otimes g_2(x,y)$, which is equivalent to $g_1(x,y) \otimes h(x,y) = g_2(x,y)$. Where h(x,y) takes the format of Gaussian function, the $FWHM_h$ of h(x,y) can be obtained as $\sqrt{FWHM_{g_2}^2 - FWHM_{g_1}^2}$. Once $FWHM_h$ is determined, $\sigma_h$ and h(x,y) are determined.

A transformation component 210 transforms the projection data $P_{n,m}$ so that similar views across different segments have approximately the same ROR. In the illustrated embodiment, this is accomplished by respectively applying $h_{n,m}$ to $P_{n,m}$, for each view of each segment, to produce $\overline{P}_{n,m}$. In other words, for all $n \in [1,N]$ and $m \in [1,M]$: $\overline{P}_{n,m}, P_{n,m} * h_{n,m}$. In the illustrated embodiment, this operation is performed in the spatial domain. However, this operation could alternatively be performed in the frequency domain using a Fast Fourier Transform (FFT) or the like.

This can be thought of as applying an additional system in the acquisition process in which the projections $\overline{P}_{n,m}$, $n \in N$, are treated as sharing the same collimator-detector response function $CDR_{ROR_{ref,m}}$ for a certain viewing angle m, which makes it possible to apply depth-dependent resolution recovery (or modeling of collimator-detector response) in reconstruction.

A segment combiner 212 suitably combines or "knits" the individual N segments of projection data into a single projection data set $\overline{P}$ for reconstruction. Since all portions in the knitted projection data share the same or very similar collimator-detector response at individual viewing angle, depth-dependent modeling of collimator-detector response functions can be applied in reconstruction.

Returning to FIG. 1, the reconstructor 116 reconstructs the combined projection data $\overline{P}$. As noted above, an iterative reconstruction technique can be employed. By way of example, an estimator generates an initial image estimate to establish an initial current image estimate of the isotope distribution. A forward projector forward projects the current estimate of the isotope distribution to produce projection estimate $P_{Calc}$. A comparator compares the projection estimate $P_{Calc}$ obtained from the forward projection process with $\overline{P}$ to generate a difference ratio. A back-projector back projects the difference ratio to the reconstruction space to update the current estimate of the isotope distribution. An image updater uses the backprojected data to generate a new image estimate, and the updated image estimate is used as the current image estimate. For depth-dependent resolution recovery, a collimator-detector response modeler uses the $ROR_{ref,m}$ as the radius of rotation at the viewing angle m ($m \in [1,M]$) to model collimator-detector responses in the forward and/or backward projection processes. Reconstruction is terminated upon satisfying reconstruction termination criterion.

As such, the system 100 employs an algorithm that accommodates single reconstruction of total-body SPECT data when resolution recovery is desirable for variant ROR's across the segments. In particular, the system models the depth-dependent collimator-detector responses during the forward and backward projection processes even when all segments use totally different ROR's. In one instance, this provides a workflow with the desirable depth-dependent resolution recovery in reconstruction.

Figure 4:
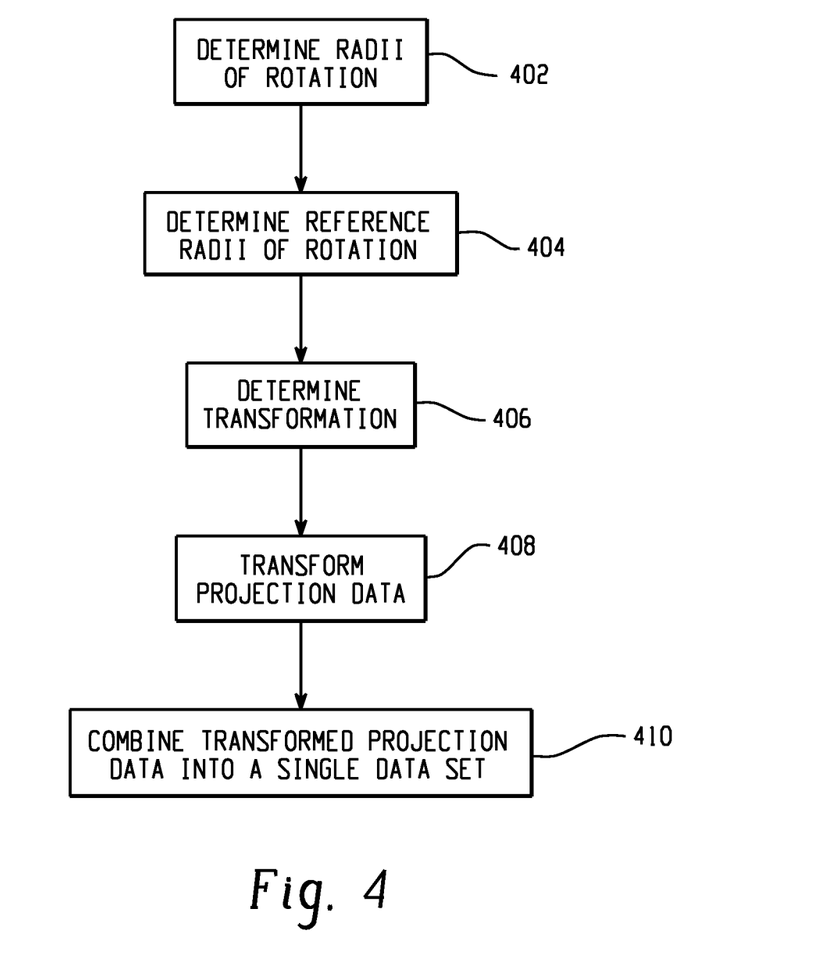
FIG. 4 illustrates a method.

Operation will now be described with reference to FIG. 4.

At 402, an $ROR_{n,m}$ is determined for each of M views for each of N segments.

At 404, a reference $ROR_{n,m}$ is determined for each of the M views across the N segments.

At 406, a transformation $h_{n,m}$ is determined for each of the M views across the N segments.

At 408, the transformation $h_{n,m}$ is applied to the projection data $P_{n,m}$ to generate $\overline{P}_{n,m}$, in which views across segments can be treated as sharing the same reference $ROR_{ref,m}$.

At 410, the projections $\overline{P}_{n,m}$ are combined to form a single set of project data $\overline{P}$, which can be reconstructed using a depth-dependent resolution recovery reconstruction algorithm and/or otherwise processed.

The above may be implemented by way of computer readable instructions, which when executed by a computer processor(s), cause the processor(s) to carry out the described techniques. In such a case, the instructions are stored in a computer readable storage medium associated with or otherwise accessible to the relevant computer. The described techniques need not be performed concurrently with the data acquisition.

Applications of the forgoing and variations thereof include, but are not limited to, SPECT as well as other medical and non-medical applications.

The invention has been described with reference to various embodiments. Modifications and alterations may occur to others upon reading the detailed description. It is intended that the invention be constructed as including all such modifications and alterations insofar as they come within the scope of the appended claims or the equivalents thereof.

The invention is claimed to be:

1. An imaging system, comprising:
  a view transformation component that includes a microprocessor configured to:
    receive single proton emission computed tomography (SPECT) acquired projection data of a subject detected with different radii of rotation in a same view across a plurality of individual segments, wherein the acquired projection data is indicative of detected gamma radiation from radionuclide decay occurring in the subject; and
    transform the acquired projection data in the same view in each of the plurality of individual segments with the different radii to projection data with a common radius of rotation;
  a segment combiner that combines the transformed projection data to produce a single data set that includes the transformed projection data in the same views across the plurality of individual segments; and
  a reconstructor that reconstructs the single data set into volumetric image data of the subject.

2. The system of claim 1, wherein the reconstructor reconstructs the single data set using a depth-dependent resolution recovery reconstruction algorithm.

3. The system of claim 2, wherein the plurality of segments include no overlap.

4. The system of claim 1, further including:
  a reference view radius of rotation selector that selects a radius of rotation from a view in one of the plurality of individual segments as a common radius of rotation for the view across the plurality of individual segments.

5. The system of claim 4, further including:
a view radius of rotation determiner that determines the radius of rotation used for each view.

6. The system of claim 4, wherein the radius of rotation selector selects the common radius of rotation by selecting a largest radius of rotation of each of the views.

7. The system of claim 4, further including:
a transformation determiner that determines a transformation for transforming the projection data of each view in a plurality of views in each segment based on the corresponding common radius of rotation for each view.

8. The system of claim 4, further including:
a transformation determiner that determines a transformation for transforming the projection data of each view in a plurality of views in each segment based on both a corresponding collimator-detector response function for each view and a collimator-detector response function for the view corresponding to the common radius of rotation.

9. The system of claim 8, further including:
a collimator-detector response function determiner that determines a collimator-detector response function for each view in a plurality of views in each segment.

10. The system of claim 1, wherein the system is part of a single photon emission computed tomography scanner with detectors configured to move tangentially with respect to an axis that extends longitudinally through an examination region, and the different radii of rotation include the distance from the longitudinal axis to the tangentially located detector, wherein the detectors are further configured to detect the gamma radiation from the radionuclide decay and produce the acquire projection data indicative of the detected gamma radiation.

* * * * *